United States Patent
Jormakka et al.

(10) Patent No.: US 12,015,221 B2
(45) Date of Patent: Jun. 18, 2024

(54) ELECTRICAL CONNECTORS FOR MEDICAL DEVICES

(71) Applicant: GE Precision Healthcare LLC, Wauwatosa, WI (US)

(72) Inventors: Jami Matti Jormakka, Espoo (FI); Joona Henrik Siivonen, Hyvinkää (FI)

(73) Assignee: GE Precision Healthcare LLC, Wauwatosa, WI (US)

( * ) Notice: Subject to any disclaimer, the term of this patent is extended or adjusted under 35 U.S.C. 154(b) by 600 days.

(21) Appl. No.: 17/203,169

(22) Filed: Mar. 16, 2021

(65) Prior Publication Data

US 2022/0302624 A1    Sep. 22, 2022

(51) Int. Cl.
| | |
|---|---|
| *H01R 13/422* | (2006.01) |
| *A61B 5/301* | (2021.01) |
| *A61B 5/308* | (2021.01) |
| *H01R 12/77* | (2011.01) |

(52) U.S. Cl.
CPC ......... *H01R 13/4223* (2013.01); *A61B 5/301* (2021.01); *A61B 5/308* (2021.01); *H01R 12/777* (2013.01)

(58) Field of Classification Search
CPC ...... H05K 1/0281; H05K 1/119; H05K 1/118; H05K 2201/056; A61B 5/308; A61B 5/301; H01R 12/777; H01R 13/4223
USPC .......................................... 439/680, 77, 496
See application file for complete search history.

(56) References Cited

U.S. PATENT DOCUMENTS

| | | | | |
|---|---|---|---|---|
| 4,784,615 A | * | 11/1988 | Teng-Hong | H01R 12/61 439/496 |
| 4,815,990 A | | 3/1989 | Ristedt | |
| 5,026,291 A | * | 6/1991 | David | H01R 12/79 439/493 |
| 5,040,997 A | * | 8/1991 | Garner | H01R 12/78 439/329 |
| 5,397,247 A | * | 3/1995 | Aoki | H01R 12/777 439/495 |
| 5,403,202 A | * | 4/1995 | Roehling | H05K 1/118 439/496 |
| 5,702,269 A | * | 12/1997 | Uchida | H01R 13/2414 439/496 |
| 6,558,186 B1 | * | 5/2003 | LePottier | H01R 12/79 439/495 |

(Continued)

OTHER PUBLICATIONS

EP patent application 22160738.5 filed Mar. 8, 2022—extended Search Report issued Aug. 11, 2022; 10 pages.

*Primary Examiner* — Marcus E Harcum
(74) *Attorney, Agent, or Firm* — Andrus Intellectual Property Law, LLP (57) ABSTRACT

An electrical connector having a main support with a front and back, top and bottom, and left and right opposite the left. Fingers extend forwardly from the front of the main support to a tip. The fingers each have a top and bottom and are arranged from left to right of the main support with gaps defined between them. A flexible circuit board has inner and outer surfaces with electrical leads on the outer surface. Openings are defined through the flexible circuit board between the electrical leads. The flexible circuit board is wrapped around the fingers such that the outer surface of the flexible circuit board is supported on both the top and the bottom of the fingers and the openings in the flexible circuit board are aligned with the gaps between the fingers.

18 Claims, 6 Drawing Sheets

(56) References Cited

U.S. PATENT DOCUMENTS

| | | | | |
|---|---|---|---|---|
| 6,626,698 B2* | 9/2003 | Matsumura | .......... | H01R 12/775 |
| | | | | 439/496 |
| 6,659,794 B2* | 12/2003 | Yamatani | ............ | H01R 13/501 |
| | | | | 439/495 |
| 6,739,903 B1* | 5/2004 | Aoki | ...................... | H01R 12/89 |
| | | | | 439/496 |
| 6,749,459 B2* | 6/2004 | Urbaniak | ................ | H01R 12/78 |
| | | | | 439/496 |
| 6,755,683 B2* | 6/2004 | Roberts | .................. | H01R 12/79 |
| | | | | 439/496 |
| 7,172,455 B2* | 2/2007 | Pabst | ..................... | H01R 12/78 |
| | | | | 439/496 |
| 7,232,334 B2* | 6/2007 | Shimizu | ............... | H01R 12/771 |
| | | | | 439/496 |
| 7,467,970 B2* | 12/2008 | Ikuta | .................... | H01R 12/592 |
| | | | | 439/496 |
| 7,530,839 B1* | 5/2009 | Lee | ...................... | H01R 12/592 |
| | | | | 439/496 |
| 9,812,801 B2* | 11/2017 | Okura | ....................... | H01B 7/08 |
| 10,756,463 B2* | 8/2020 | Hiroki | .................... | H01R 35/04 |
| 2003/0008549 A1* | 1/2003 | Matsumura | ............ | H05K 1/118 |
| | | | | 439/494 |
| 2011/0147062 A1 | 6/2011 | Stevenson | | |
| 2014/0066741 A1 | 3/2014 | Peterson | | |
| 2019/0173234 A1 | 6/2019 | Xu | | |

\* cited by examiner

ELECTRICAL CONNECTORS FOR MEDICAL DEVICES

FIELD

The present disclosure generally relates to electrical connectors for medical devices, and more particularly to disposable electrical connectors for leadwires for medical devices.

BACKGROUND

Medical devices in the field often include a host device providing a display of data and controls of the device, as well as a peripheral device that somehow engages with the patient to collect this data for display. The peripheral device in many cases is connected by a leadwire to the host device, and particularly by an electrical connector of the leadwire being receivable within an input port of the host device. This allows the peripheral device to be removable from the host device for ease of replacement due to damage, or to enable disposable peripheral devices and/or leadwires for convenience and/or sanitation purposes.

Section 4.2.1 of AAMI EC53 standard refers to the DIN 42-802 standard for ECG leadwire connector requirements to mitigate the potential hazard of a patient connected leadwire inadvertently making electrical contact with the power mains or other hazardous voltage sources. The DIN 42-802 standard specifies that a standard test probe such as a finger not be able to make electrical contact with the ECG leadwire connector pins (or sockets) when applied with a force of 30 N (6.744 lbs.). Section 8.5.2.3 of the AAMI ES60601-1 2005 Cl 2009 has similar requirement except the test probe force is reduced to 10 N (2.248 lbs.). Section 8.9.1.15 relates to creepage distances and air clearances for defibrillation-proof applied parts. IEC 60601-1 standard requires 1.0 mm (0.039 in.) creepage distance, 0.5 mm (0.0196 in.) of air clearance, and a dielectric strength of 1,500 Vac for at least 1 minute, protection from mains voltage. Defibrillation patient safety requirements of AAMI EC11:1991/(R)2001 (section 3.2.14.2.2) dictate that the reduction in energy delivered to a patient being defibrillated be less than 10% of the total energy delivered by the defibrillator while an electrocardiograph and its associated leadwires are attached to the patient in order to maintain the efficacy of defibrillation. The defibrillator generates voltages of up to 5000V peak, therefore, in order to prevent "arcing" of defib energy shunting around the patient, the leadwires and the connector must maintain adequate electrical isolation (i.e., withstand 5000V peak). In order to guarantee this level of isolation a 8.0 mm (0.314 in.) creepage distance, 4.0 mm (0.157 in.) of air clearance must be maintained in order to support a dielectric breakdown strength of 5,000 volts between the exposed conductive surfaces of the connector. These dimensional requirements are based upon the assumptions of a pollution degree 2 level, using materials with a comparative tracking index (CTI) greater than 175 for the substrate, at an altitude less than 2000 meters above sea level. The non-exposed conductor areas of the connector/leadwire must also be constructed to support the 5,000 volt withstand level by incorporating appropriate conductor spacing's based upon the specific dielectric materials in between them.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

One embodiment of the present disclosure generally relates to an electrical connector for a medical device. The connector includes a main support having a front and a back opposite the front, a top and a bottom opposite the top, and a left and a right opposite the left. Fingers each extend forwardly from the front of the main support to a tip, where the fingers have a top and a bottom opposite the top, and where the fingers are arranged from the left to the right of the main support such that gaps are defined between the fingers. A flexible circuit board has an outer surface and an inner surface opposite the outer surface, where the flexible circuit board includes electrical leads on the outer surface thereof, where openings are defined through the flexible circuit board between the electrical leads, and where the flexible circuit board is wrapped around the fingers such that the outer surface of the flexible circuit board is supported on both the top and the bottom of the fingers and the openings in the flexible circuit board are aligned with the gaps between the fingers.

In certain embodiments, a finger height is defined between the tops and bottoms of the fingers. Walls sandwich each of the fingers, where the walls each have a top and a bottom opposite the top that define a wall height therebetween, where the walls extend away from the main support to a front edge, and where at least one of the wall height of each of the walls is greater than the finger height of each of the fingers and the front edges of the walls extends farther than the tips of the fingers from the main support.

In certain embodiments, the wall height of each of the walls is a height difference greater than the finger height of each of the fingers, and the front edges of the walls extends farther than the tips of the fingers from the main support by a front difference.

In certain embodiments, the front difference is different than the height difference.

In certain embodiments, main support walls among the walls are coupled to the left and the right of the main support, the main support walls each having a top and a bottom opposite the top that define a main support wall height therebetween, where a main support height is defined between the top and the bottom of the main support, and where the main support wall height is greater than the main support height.

In certain embodiments, the main support walls are coplanar with two of the walls, where the wall heights equal the main support wall heights.

In certain embodiments, the main support walls extend from the front of the main support only partially towards the back of the main support.

In certain embodiments, the flexible circuit board has a main section and a moveable section that extends forwardly from the main section to a board edge, the main section being supported by the main support when the flexible circuit board is wrapped around fingers, where the openings defined through the flexible circuit board have a front boundary that is closer than the board edge to the main section along the outer surface of the flexible circuit board.

In certain embodiments, a lock opening is defined through the flexible circuit board, where the lock opening is closer than the board edge to the main section along the outer surface of the flexible circuit board. A lock protrusion extends away from the bottom of the main support, where when the flexible circuit board is wrapped around the fingers the lock protrusion of the main support is received within the lock opening defined in the flexible circuit board.

In certain embodiments, each of the gaps has a gap width between the fingers, where the lock opening has a lock opening width extending substantially parallel to the gap widths, and where the lock opening width is greater than each of the gap widths.

In certain embodiments, the flexible circuit board has a main section and a moveable section that extends forwardly from the main section to a board edge, the main section being supported by the main support when the flexible circuit board is wrapped around fingers, where the openings defined through the flexible circuit board have a front boundary that is closer than the board edge to the main section along the outer surface of the flexible circuit board.

In certain embodiments, the electrical leads extend from first to second ends, where the first ends are positioned on the fingers when the flexible circuit board is wrapped around the fingers.

In certain embodiments, each of the electrical leads has an exposed contact between the first and second ends configured for electrically engaging with the medical device, and the exposed contacts are positioned on the tips of the fingers when the flexible circuit board is wrapped around the fingers.

In certain embodiments, the flexible circuit board has a main section and a moveable section that extends forwardly from the main section to a board edge, the main section being supported by the main support when the flexible circuit board is wrapped around fingers, where the openings defined through the flexible circuit board have a front boundary that is closer than the board edge to the main section along the outer surface of the flexible circuit board, and where the front boundaries of the openings defined in the flexible circuit board are closer than the first ends of the electrical leads to the board edge.

In certain embodiments, the fingers comprise at least five fingers that are coplanar with each other and with the main support.

In certain embodiments, the flexible circuit board is a flexible printed circuit board having exposed contacts, and wherein the inner surface of the flexible printed circuit board is free of exposed contacts.

In certain embodiments, the exposed contacts are all a same distance from the front of the main support along the outer surface when the flexible circuit board is wrapped around fingers.

Another embodiment generally relates to a method for making an electrical connector for a medical device. The method includes forming a main support having a front and a back opposite the front, a top and a bottom opposite the top, and a left and a right opposite the left. The method includes forming fingers that each extend forwardly from the front of the main support to a tip, wherein the fingers have a top and a bottom opposite the top with a finger height defined therebetween. The method includes forming walls that sandwich each of the fingers, where the fingers are arranged from the left to the right of the main support such that gaps are defined between the fingers, where the walls each have a top and a bottom opposite the top that define a wall height therebetween, where the walls each extend away from the main support to a front edge, and where the wall height of each of the walls is greater than the finger height of each of the fingers and the front edges of the walls extends farther than the tips of the fingers from the main support. The method includes forming a flexible circuit board having an outer surface and an inner surface opposite the outer surface to have electrical leads on the outer surface thereof, where the flexible circuit board has a main section and a moveable section. The method includes defining openings through the flexible circuit board between the electrical leads. The method includes positioning the main section of the flexible circuit board on the main support and folding the moveable section of the flexible circuit board around the fingers, where the flexible circuit board is wrapped around the fingers such that the flexible circuit board is supported on both the top and the bottom of the fingers and the openings in the flexible circuit board are aligned with the gaps between the fingers.

In certain embodiments, the flexible circuit board has a main section and a moveable section that extends forwardly from the main section to a board edge. A lock opening is defined through the flexible circuit board to be closer than the board edge to the main section along the outer surface of the flexible circuit board. A lock protrusion extends away from the bottom of the main support, where when the flexible circuit board is wrapped around the fingers the lock protrusion of the main support is received within the lock opening defined in the flexible circuit board, where the electrical leads extend from first to second ends, where the first ends are positioned on the fingers when the flexible circuit board is wrapped around the fingers, where each of the electrical leads has an exposed contact between the first and second ends configured for electrically engaging with the medical device, and where the exposed contacts are positioned on the tips of the fingers when the flexible circuit board is wrapped around the fingers.

Another embodiment generally relates to an electrical connector for a medical device, the connector having a main support with a front and a back opposite the front, a top and a bottom opposite the top, and a left and a right opposite the left, where a lock protrusion extends away from the bottom of the main support. Fingers extend forwardly from the front of the main support to a tip, where the fingers have a top and a bottom opposite the top, where a finger height is defined between the tops and bottoms of the fingers, where the fingers are arranged from the left to the right of the main support such that gaps are defined between the fingers, and where the fingers are coplanar with each other and with the main support. Walls sandwich each of the fingers, where the walls each have a top and a bottom opposite the top that define a wall height therebetween, where the walls extend away from the main support to a front edge, and where at least one of the wall height of each of the walls is greater than the finger height of each of the fingers and the front edges of the walls extends farther than the tips of the fingers from the main support, where the wall height of each of the walls is greater than the finger height of each of the fingers, and where the front edges of the walls extends farther than the tips of the fingers from the main support. A flexible circuit board has an outer surface and an inner surface opposite the outer surface, where the flexible circuit board has a main section and a moveable section that extends forwardly from the main section to a board edge, where the flexible circuit board includes electrical leads that are exposed on the outer surface thereof, where openings are defined through the flexible circuit board between the electrical leads, and where the flexible circuit board is wrapped around the fingers such that the outer surface of the flexible circuit board is supported on both the top and the bottom of the fingers and the openings in the flexible circuit board are aligned with the gaps between the fingers, where a lock opening is defined through the flexible circuit board, where the lock opening is closer than the board edge to the main section along the outer surface of the flexible circuit board, and where when the flexible circuit board is wrapped around the fingers the lock protrusion of the main support is received within the lock opening defined in the flexible circuit board.

Various other features, objects and advantages of the disclosure will be made apparent from the following description taken together with the drawings.

BRIEF DESCRIPTION OF THE DRAWINGS

The present disclosure is described with reference to the following drawings.

DETAILED DISCLOSURE

The present inventors have identified that electrical connectors presently known in the art, and particularly those for disposable peripheral devices including flexible printed circuit boards, are susceptible to water ingress and contamination. Due to the flat surfaces, the appropriate creepage and air clearances are difficult to achieve, thereby resulting in large and heavy electrical connectors. Likewise, the flatform factor limits the direction of the electrical contact points for meeting within the corresponding input ports, and the flat and wide connectors having open contact pads make them hard to protect against making contact with non-flat surfaces. Through experimentation and development, the inventors have developed the presently disclosed electrical connectors, which overcome the problems discussed above.

Figure 1:
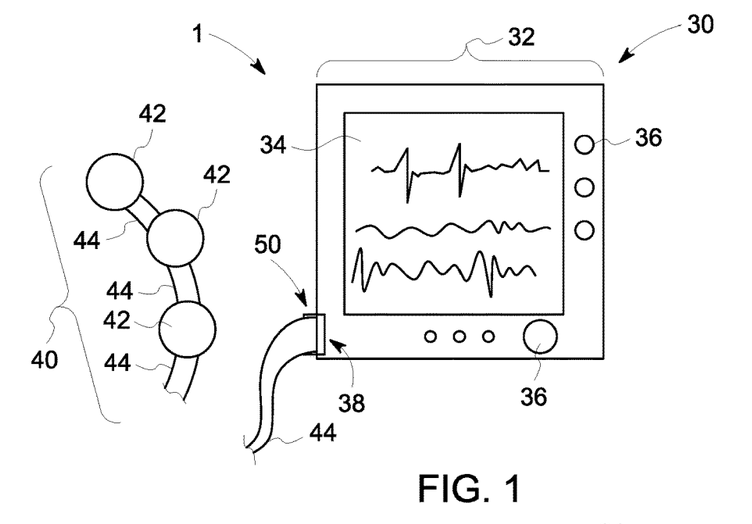
FIG. 1 is a front view of a medical device including a peripheral device having a leadwire with an electrical connector receivable by a host device according to the present disclosure.

FIG. 1 depicts an exemplary medical device 30 as generally known in the art, but now incorporating a system 1 according to the present disclosure. The medical device 30 includes a host device 32 having a display 34, controls 36, and input port 38, whereby the input port 38 provides a basis for connecting the host device 32 to a peripheral device 40. In the example shown, the peripheral device 40 is a disposable neuromuscular transmission device having three electrodes 29 configured for positioning on a patient, such as GE Healthcare's NMT Module Entropy Sensor. The electrodes 42 are coupled together by leadwires 44, which through the electrical connector 50 presently disclosed is receivable within the input port 38 of the host device 32 to provide communication between the host device 32 and peripheral device 40. Other exemplary peripheral devices 40 include GE Healthcare's MAC VU360 Resting ECG or CASE Exercise testing system, for example. Non-healthcare applications for the presently disclosed electrical connector 50 are also contemplated by the present disclosure, such as consumer electronics.

Figure 2:
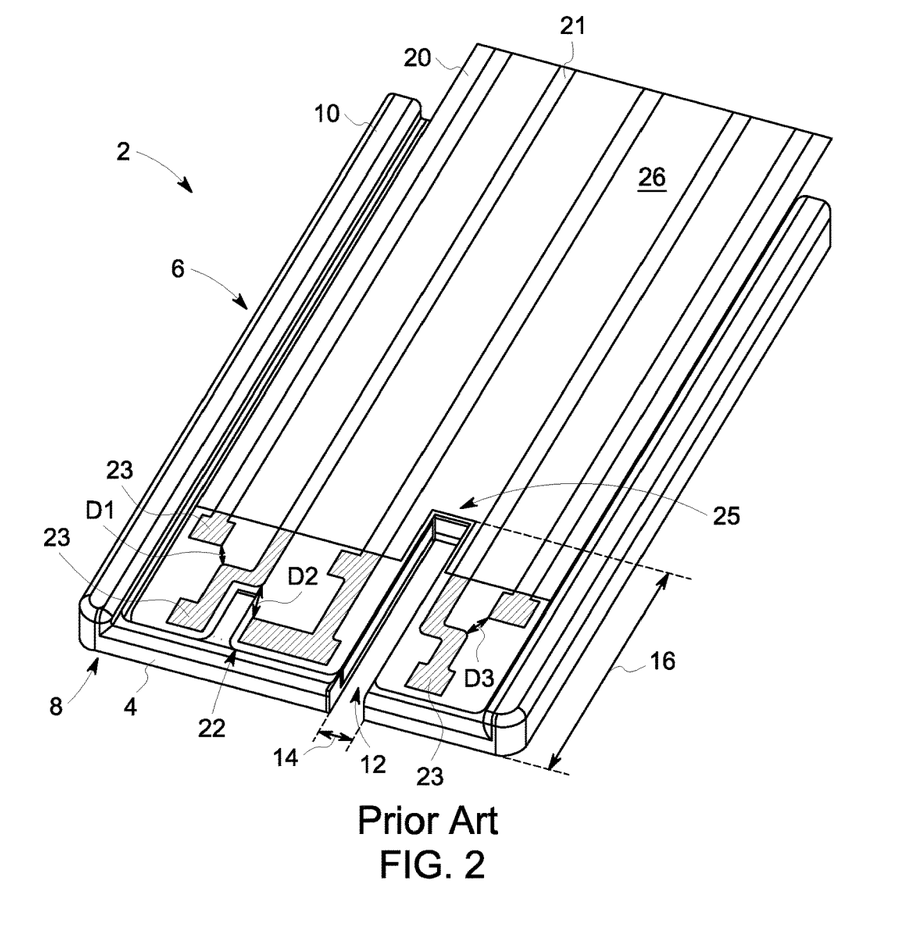
FIG. 2 is a top perspective view of an electrical connector as presently known in the art.

FIG. 2 depicts a prior art connector 2 as presently known in the art. The front 4 of the prior art connector 2 is configured to be inserted in an input port similar to the input port 38 of FIG. 1, but specifically configured to correspond to the prior art connector 2. The prior art connector 2 has a top 6 and opposite bottom 8 and is comprised of a rigid portion 10 with a flexible circuit board 20 positioned on top. A slot 12 is defined through the rigid portion 10 and extends rearwardly from the front 4, the slot 12 having a width 14 and length 16. The slot 12 is used in part to provide electrical isolation between two separate functions in the same applied part (e.g., transmitting signals or receiving signals), or between different functions. For example, in the case of neuromuscular transmission (NMT), the slot 12 provides that patient stimulating current is separated from the sensor electromyograph (EMG) electrodes. By having this slot 12, a large air clearance can be achieved when the electrical connector 50 is mated with the input port 38 of the host device 32. In some applications, the creepage distance requirement can be greater that the required air clearance, especially if moisture/pollution is present inside the electrical connector 50. The slot 12 will separate two halves of the electrical connector 50 from each other so that the creepage distance is significantly greater. In addition, the slot 12 can and or alternatively function as a poke-yoke, ensuring that the electrical connector 50 is inserted into the input port 38 in the intended orientation. The flexible circuit board 20 has a front 22 substantially aligned with the front 4 of the prior art connector 2, which also has a slot 25 that substantially overlays the slot 12 of the rigid portion 10.

Similar to other flexible circuit boards presently known in the art, the flexible circuit board 20 includes a plurality of leads 21 running through the flexible circuit board 20, which terminate at exposed contacts 23 near the front 22 of the flexible circuit board 20. In the example shown, distances D1, D2, and D3 are shown between the exposed contacts 23, particularly denoting the shortest distances between these exposed contacts 23. A slot 24 is also defined within the flexible circuit board 20, which in the present example is intended to increase separation between two of the exposed contacts 23 in view of the regulations regarding clearances.

This prior art connector 2 is subject to the problems described above, including being susceptible to water ingress and contamination from the configuration of the exposed contacts. Likewise, the configuration is limited in terms of how many exposed contacts 23 may be positioned on the prior art connector 2 due to creepage and air clearance requirements, which are nonetheless separated by relatively small distances D1-D3. In the example shown, the exposed contacts 23 are a minimum of 2.0 mm apart from each other. The prior art connector 2 is also limited in that the exposed contacts 23 must be positioned on the top 6 of the prior art connector 2, limiting the manner in which these exposed contacts 23 may make contact with the host device via the corresponding input port. Moreover, as is apparent from the view of FIG. 2, the inventors have recognized that it is hazardously simple to make electrical contact between exposed contacts 23 in this configuration, for example via accidental contact with conductive objects.

Accordingly, the present inventors have developed an alternative electrical connector that mitigates against the electrical hazards presently known of flexible circuit board type connectors in the art. The presently disclosed connectors also advantageously provide a cost-effective design and a compact form factor while nonetheless fulfilling the safety requirements and considerations described above.

Figure 3A:
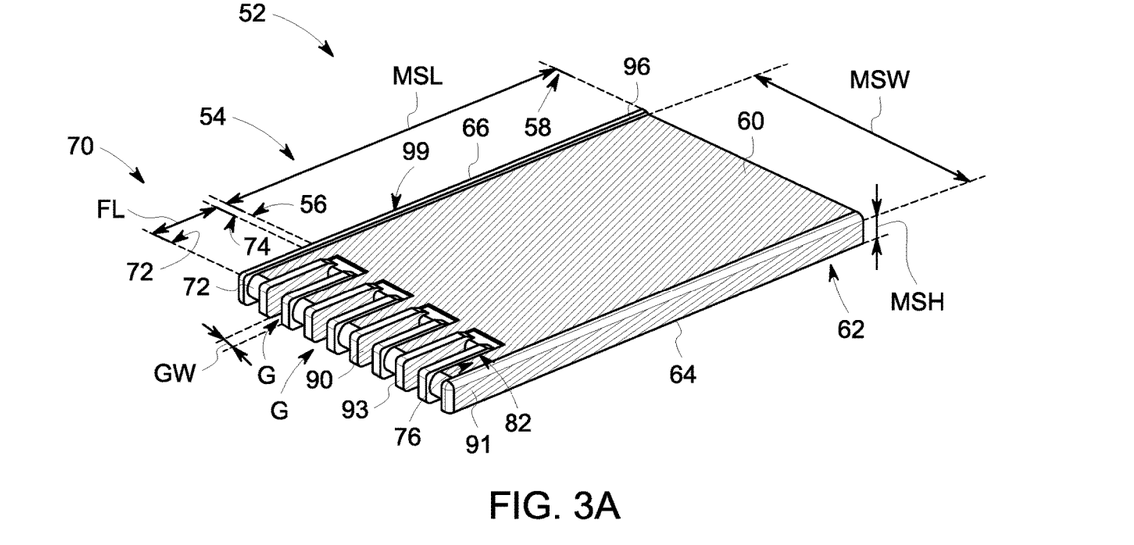
FIGS. 3A and 3B are top perspective and bottom perspective views of a rigid base with an exemplary electrical connector according to the present disclosure.
Figure 3B:
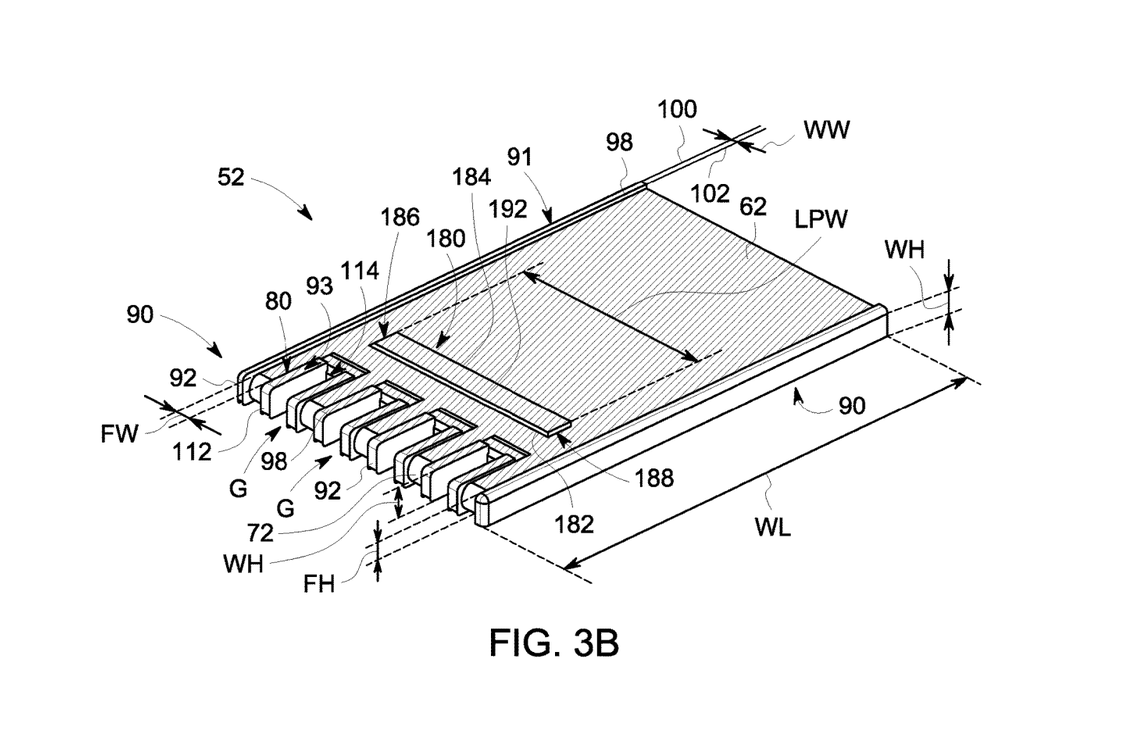
Figure 4A:
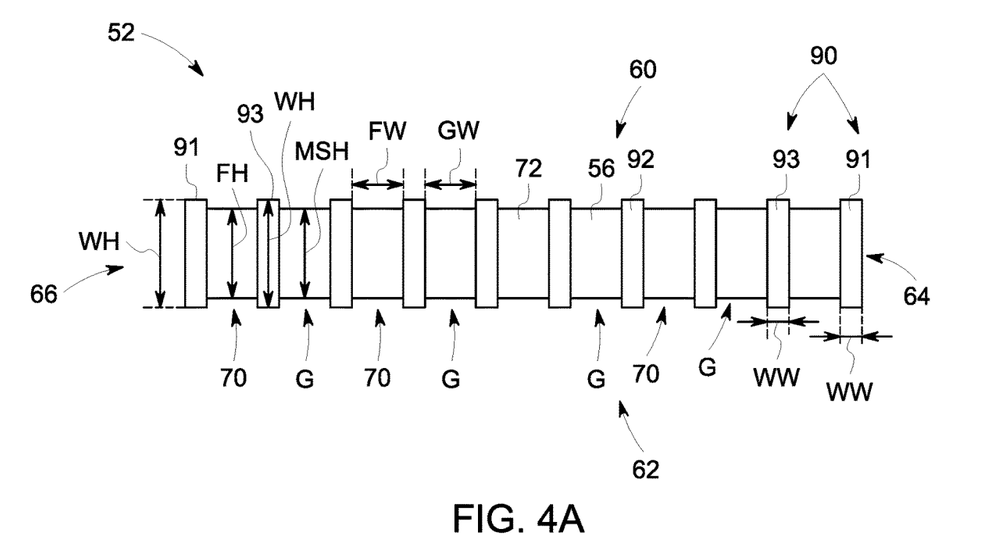
FIGS. 4A and 4B are front and top views of the exemplary rigid base of FIGS. 3A and 3B.
Figure 4B:
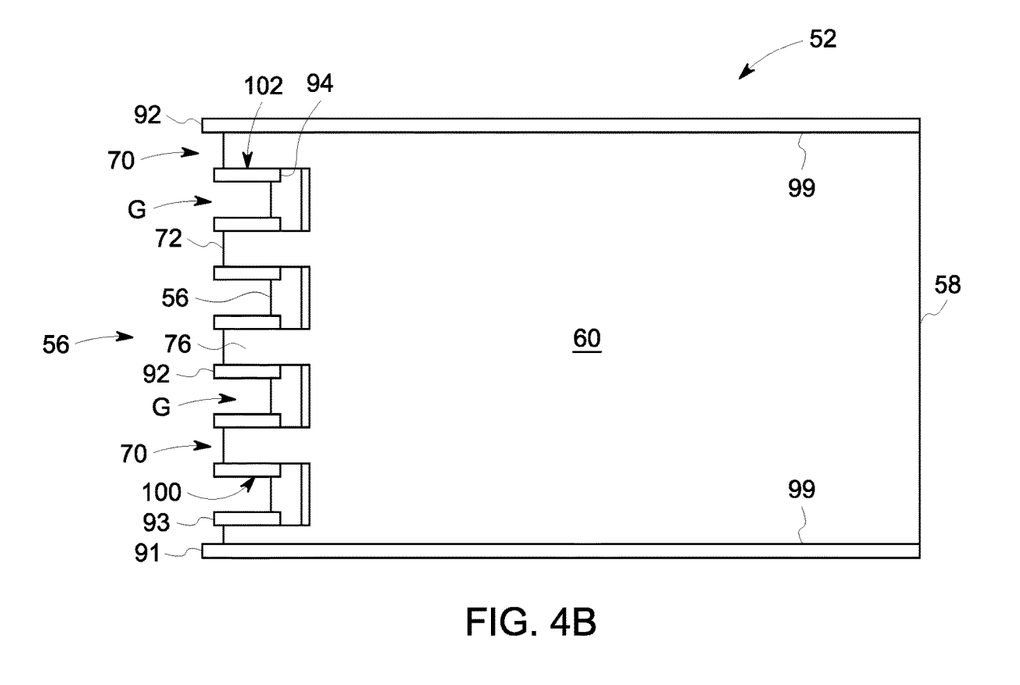

The presently disclosed electrical connector 50 is generally formed of a rigid base and a flexible circuit board, each of which is discussed in detail separately. FIGS. 3A-3B depict an exemplary rigid base 52 for an electrical connector 50 according to the present disclosure. The rigid base 52 includes a main support 54 that extends between a front 56 and back 58 defining a main support line MSL therebetween, top 60 and bottom 62 defining a main support height MSH therebetween, and left 64 and right 66 defining a main support width MSW therebetween. Fingers 70 extend forwardly from the front 56 of the main support 54, shown here in a configuration having five fingers 70. The fingers 70 each extend between a tip 72 and base end 74 defining a finger length FL therebetween, a top 76 and a bottom 78 defining a finger height FH therebetween, and a left 80 and right 82 defining a finger width FW therebetween. In this manner, a gap G and a gap width GW is formed between adjacent fingers 70 that extend forwardly from the main support 54. The rigid base 52 may be formed of different rigid polymers, ceramics, or other materials, such as polybutylene terephthalate (PBT) or any type of material providing sufficient mechanical durability and electrical insulating properties, for example. In certain embodiments, the fingers are integrally formed with the main support 54. However, it should be recognized that the fingers 70 may also or alternatively be coupled to the main support 54 through methods presently known in the art, including the use of epoxies, for example.

In certain embodiments, such as that shown in the embodiments of FIGS. 3A-3B, the rigid base 52 further includes walls 90, which include outer walls 91 and/or inner walls 93. These walls 90 extend from a front edge 92 and back 94 defining a wall length WL therebetween, a top 96 and a bottom 98 defining a wall height WH therebetween, and a left 100 and right 102 defining a wall width WW therebetween. In the embodiment shown, the walls 90 are shown to sandwich the fingers 70. The present example also shows a main support wall 99 that extends rearwardly from the walls 90, whereby in certain examples the main support wall 99 is aligned with the main support 54 and, with the other walls 90 (and particularly inner walls 93) align with the fingers 70. In the embodiment shown, the wall height WH is greater than the finger height FH, as well as the main support height MSH. Likewise, the walls 90 are shown to extend forwardly from the tips 72 of the fingers 70. The tips 72 are shown here to has a side profile that is substantially semi-circular to minimize stresses on the flexible circuit board 130 (discussed below). However, it will be recognized that other shapes for the tips 72 are also contemplated by the present disclosure. In an exemplary embodiment, a front difference between the front edge 92 of the walls 90 and the tips 72 of the fingers 70 provides ≥0.5 mm distance from the exposed contact 23 to a flat surface, as specified in IEC60601-1 clause 8.5.2.3, in addition the walls 90 protect the exposed contact 23 from making a connection with test finger. Likewise, in certain embodiments, a height difference between the wall height WH of the walls 90 and the finger height FH of the fingers 70 is the same as discussed above with respect the front difference (between the front edge 92 of the walls 90 and the tips 72 of the fingers 70).

In certain embodiments, such as that shown in FIGS. 3A-3B, the wall heights WH of the outer walls 91, inner walls 93, and main support walls 99 are shown to be the same. However, it should be recognized that differences in the wall heights WH are also contemplated by the present disclosure. Likewise, the present disclosure contemplates configurations in which the front edge 92 of the outer walls 91 extends a different distance from the front 56 of the main support 54 than that of the inner walls 93. Likewise, the present disclosure contemplates configurations in which the main support walls 99 are not coplanar with the outer walls 91.

With reference to FIG. 3B, the rigid base 52 further includes a lock protrusion 180 extending downwardly from the bottom 62 of the main support 54. The lock protrusion 180 extends between a front 182 and back 184, between a left 186 and right 188 defining a left protrusion width LPW therebetween, and a bottom 192 extending from the main support 54 by a lock protrusion height LPH. The lock protrusion 180 may be coupled to the main support 54 or integrally formed therewith, for example. In the example shown, the lock protrusion 180, and particularly the bottom 192 thereof has a rectangular shape and is parallel to the bottom 62 of the main support 54. However, it should be recognized that different shapes for the bottom 192 of the lock protrusion 180, and also alternate planes thereof, are contemplated by the present disclosure. Additional detail regarding the lock protrusion 180 is provided below.

Figure 5A:
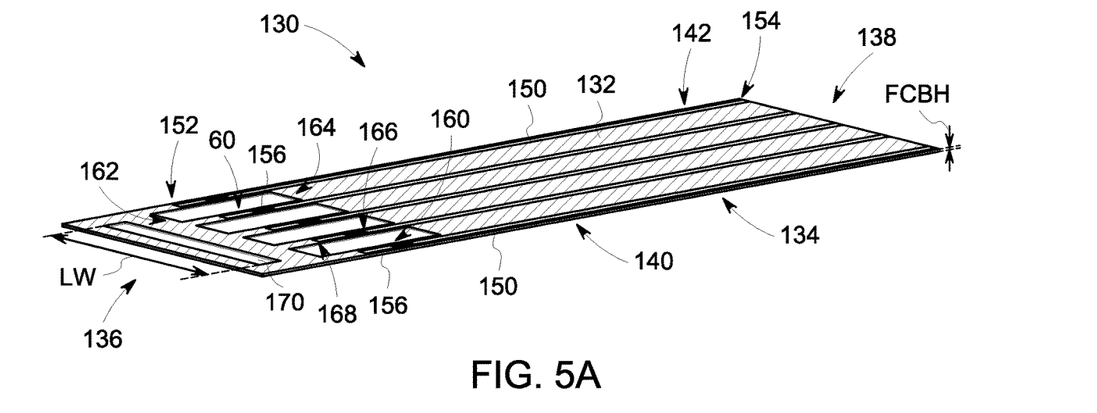
FIGS. 5A and 5B are top perspective and bottom perspective views of a flexible circuit board supported on the rigid base of FIGS. 3A and 3B according to the present disclosure.
Figure 5B:
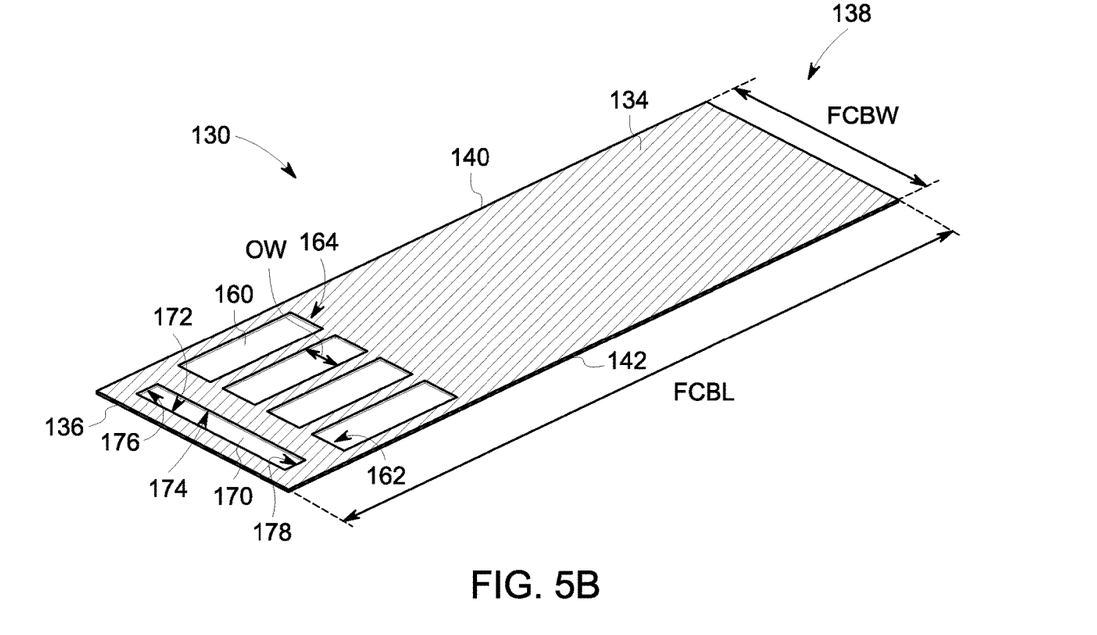

FIGS. 5A and 5B depict an exemplary embodiment of flexible circuit board 130 for integration within an electrical connector 50 according to the present disclosure. The flexible circuit board may be formed of commercially available materials, such as a conductive (e.g. silver/carbon) traces printed on Polyethylene terephthalate PET film. The traces are insulated by printing a dielectric layer on top of the traces, except for the exposed contact 23 on the tip 72 of the finger 70. The flexible circuit board 130 is presently shown before being assembled with the rigid base 52, such as the rigid base 52 previously shown in FIGS. 3A-3B. The flexible circuit board 130 has an outer surface 132 and inner surface 134 defining a flexible circuit board height FCBH therebetween, a board edge 136 and back 138 defining a flexible circuit board length FCBL therebetween, and a left 140 and right 142 defining a flexible circuit board width FCBW therebetween. Electrical leads 150 are defined within the flexible circuit board 130 in a manner known in the art and extend between a first end 152 and a second end 154. Exposed contacts 156 are provided between the first end 152 and second end 154, substantially near to the first end 152. Communication with the electrical leads 150 may be made via the exposed contacts 156, which is propagated along the corresponding electrical leads 150 to communicate with the peripheral device in a manner known in the art.

Openings 160 are defined within the flexible circuit board 130 between the first ends 152 of the electrical leads 150. Each opening 160 is defined by a front boundary 162 and back boundary 164, the front boundary 162 being closer than the back boundary 164 to the board edge 136. The openings 160 are further defined between a left 166 and a right 168 with an opening width OW defined therebetween. The present inventors have identified that by positioning these openings 160 between the electrical leads 150, and particularly the exposed contacts 156 associated therewith, the exposed contacts 156 may be positioned closer together than without the openings 160 while remaining in compliance with regulations regarding creepage and air clearance.

In the embodiment shown, a lock opening 170 is also defined through the flexible circuit board 130, in this example near to the board edge 136 of the flexible circuit board 130 than the openings 160. In the configuration shown, the lock opening 170 is formed as a substantially rectangular shape having a front 172 and back 174, as well as a left 176 and right 178 defining a lock width LW therebetween. As will become apparent, the distances between the electrical leads 150 correspond to the distances between the fingers 70, and likewise the lock opening 170 and its lock width LW corresponds to the lock protrusion 180 and its lock protrusion width LPW.

Figure 6A:
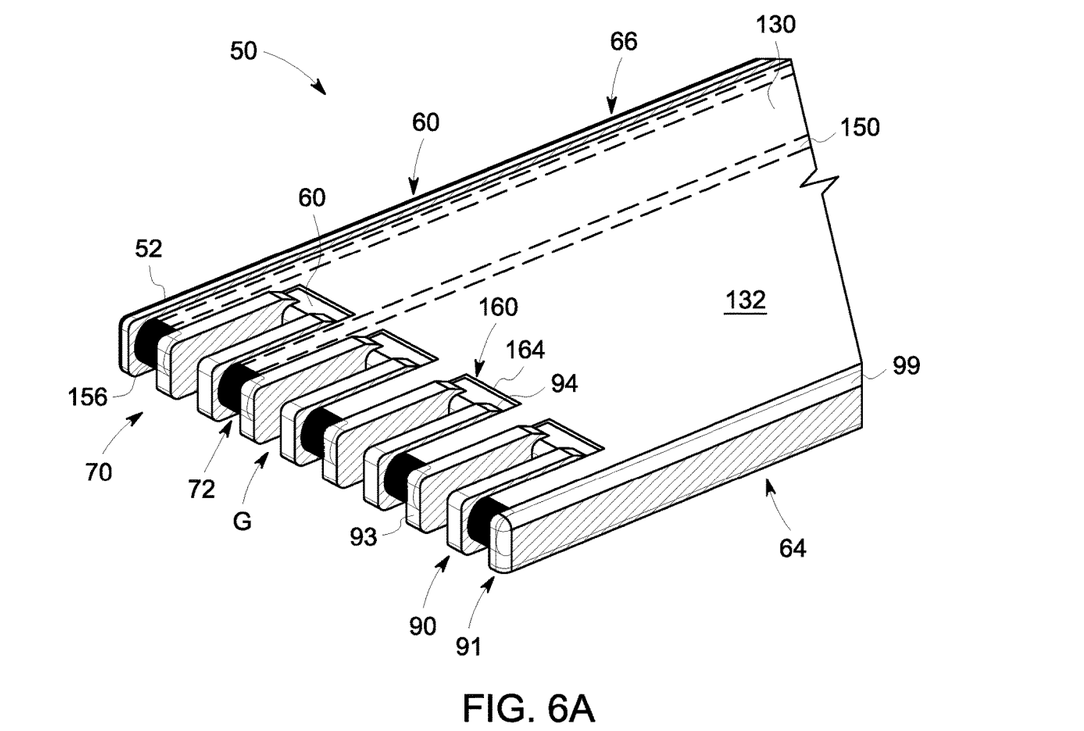
FIGS. 6A and 6B are top perspective and bottom perspective views of the flexible circuit board of FIGS. 5A and 5B assembled with the rigid base of FIGS. 3A and 3B to form an exemplary electrical connector according to the present disclosure.
Figure 6B:
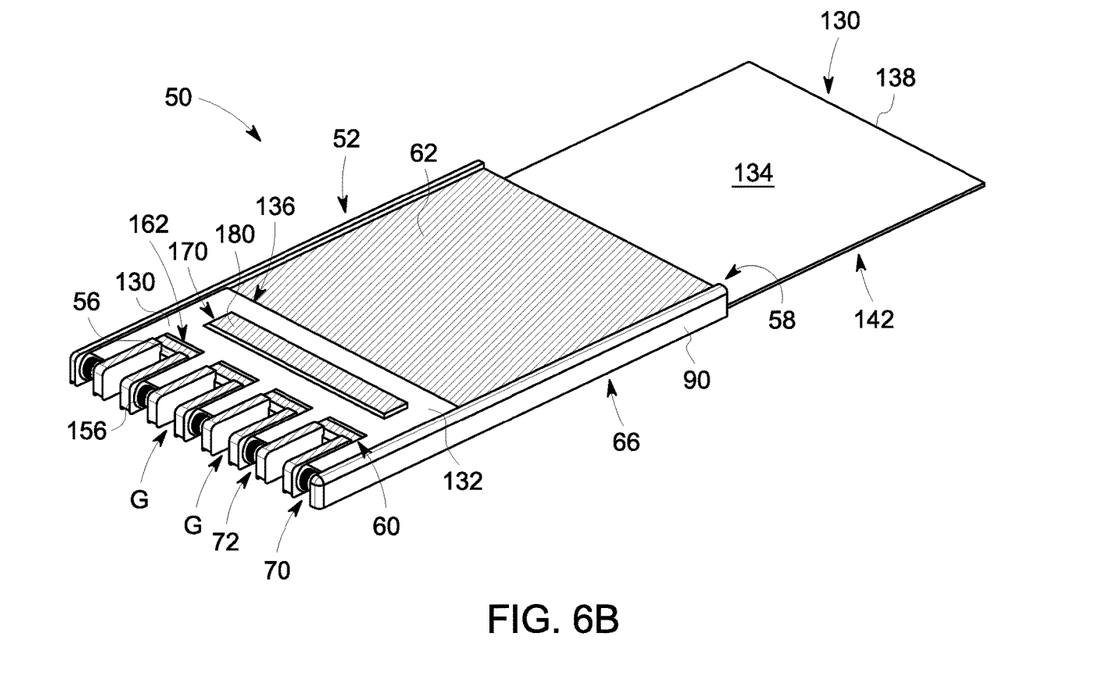

FIGS. 6A and 6B depict a flexible circuit board 130 such as that shown in FIGS. 5A-5B coupled to a rigid base 52 such as that disclosed in FIGS. 3A-4B, and particularly wrapped around the tips 72 of the fingers 70. As shown, the openings 160 of the flexible circuit board 130 overlay with the gaps G defined between the fingers 70 of the rigid base 52. In the example shown, the openings 160 are sized to not only accommodate the open space of the gaps G, but also the walls 90 sandwiching each of the fingers 70. In this manner, the openings 160 are sized sufficiently large to not interfere with these walls 90, such as depicted by the back 94 of the walls 90 shown in FIG. 6A being forward of the back boundary 164 of the opening 160, for example.

As also shown in FIGS. 6A and 6B, the exposed contacts 156 of the electrical leads 150 defined in the flexible circuit board 130 are now aligned with the tips 72 of the fingers 70, whereby in the present example the exposed contacts 156 face forwardly from these tips 72. However, it should be recognized that the present disclosure contemplates configurations in which the position of the exposed contact 156 may face any desired direction, including entirely upwardly or parallel to the top 60 of the main support 54, entirely downwardly, or parallel to the bottom 62 of the main support 54, or any angle therebetween. This allows the electrical connector 50 to be configured in a manner to protect the exposed contacts 156, and also in the advantageous configuration in which inserting the electrical connector 50 into the input port 38 of the host device 32 (see FIG. 1) forms contacts with the exposed contacts 156 in the same direction of the insertion of the electrical connector 50, as discussed further below. In other words, the present inventors have recognized particular advantages in the present design of the electrical connector 50, including that the exposed contacts 156 are normal to the tips 72 of the fingers 70.

As shown in FIG. 6A, the walls 90 assist in retaining the flexible circuit board 130 in proper position on the rigid base 52, as do the main support walls 99. In addition to this alignment guide and protection for the left 140 and right 142 of the flexible circuit board 130 may be adhered or otherwise coupled to the rigid base 52 in a manner presently known in the art.

As shown in FIG. 6B, the lock opening 170 of the flexible circuit board 130 is also configured to receive and retain the lock protrusion 180 extending downwardly from the rigid base 52 therein. In this manner, the lock opening 170 and lock protrusion 180 further assist in positioning the flexible circuit board 130 relative to the rigid base 52, in this example defining the position of the exposed contact 156 relative to the tips 72 of the fingers 70 to ensure proper alignment. As discussed above, the lock protrusion 180 and lock opening 170 may be shaped differently to provide this same functionality, for example being shaped in a triangular fashion, or having multiple lock protrusions 180 received within multiple lock openings 170, for example.

In this manner, the electrical connectors 50 disclosed herein provide increased resistance against contamination and water ingress, and also enable increased creepage distances and air clearances in a compact form factor. This is achieved by separating the exposed contacts 156 by the gaps G, and also walls 90. This provides high separations distances between the exposed contacts 156, while nonetheless enabling the electrical leads 150 to be located tightly together when insulated. Gaskets may also be provided on the electrical connectors 50 to provide a seal between the electrical connectors 50 and the host device 32 and/or peripheral device 40 to further prevent contamination and water ingress (the gaskets being made of rubber or polymers known in the art, for example). The present inventors have also recognized that the presently disclosed electrical connectors 50 advantageously provides reliable means to prevent connector pads coming into contact with other surfaces with having external electrical potentials.

Figure 7:
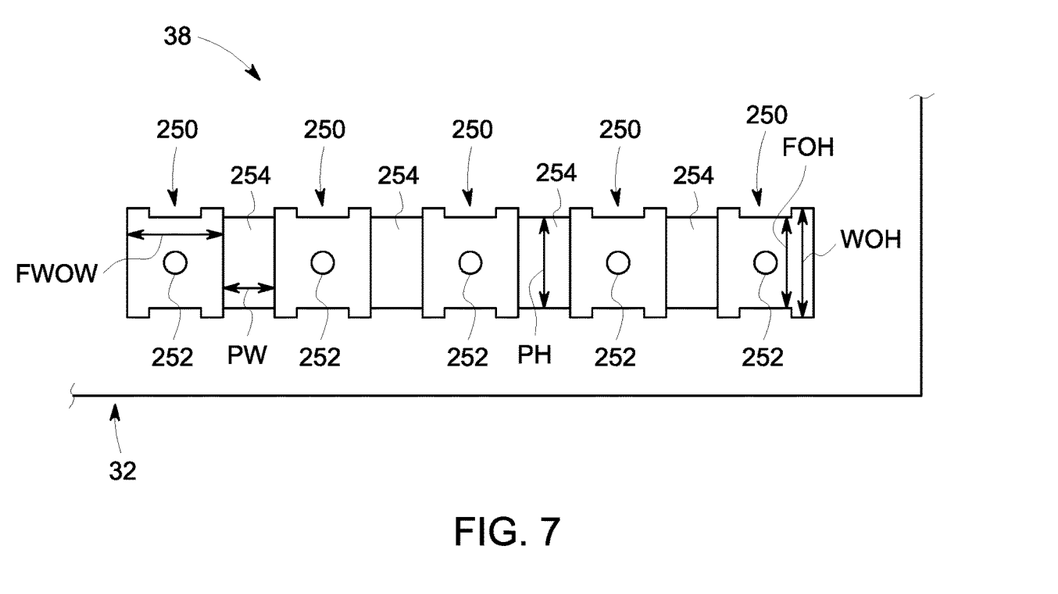
FIG. 7 is a front view of an input port for receiving an electrical connector according to the present disclosure, as may be provided within the side of the medical device shown in FIG. 1.

FIG. 7 depicts an exemplary input port 38 as may be provided in a host device 32 for receiving an electrical connector 50 according to the present disclosure. In the embodiment shown, the input port 38 includes finger openings 250 configured to receive the fingers 70 of the electrical connector 50, and in this case also the walls 90 sandwiching the fingers 70. In the example shown, the finger opening 250 includes a finger wall opening width FWOW configured to be sufficiently wide to accept two walls 90 and a finger 70 therein, and also extends between a finger opening height FOH corresponding to the finger height FH of the finger 70, and a wall opening height WOH corresponding to the wall height WH of the wall 90. A contact 252 is provided at the back of each finger opening 250, which may be spring metal or a biased conductive material as presently known in the art for engaging with the exposed contact 156 of the flexible circuit board 130 when the electrical conductor 50 is received within the input port 38.

In the embodiment shown, projections 254 extend forwardly from the input port 38 to define separation between the finger openings 250, which in the present example have a projection width PW approximately corresponding to the gap width GW of the gaps G between the fingers 270, also accommodating for any walls 90 therebetween.

In this manner, the system 1 presently disclosed (see FIG. 1) includes an input port 38 corresponding to the electrical connector 50 to together provide connectivity between a peripheral device such as the peripheral device 40 shown in FIG. 1 and the host device 32.

Certain aspects of the present disclosure are described or depicted as functional and/or logical block components or processing steps, which may be performed by any number of hardware, software, and/or firmware components configured to perform the specified functions. For example, certain embodiments employ integrated circuit components, such as memory elements, digital signal processing elements, logic elements, look-up tables, or the like, configured to carry out a variety of functions under the control of one or more processors or other control devices. The connections between functional and logical block components are merely exemplary, which may be direct or indirect, and may follow alternate pathways.

Figure 8:
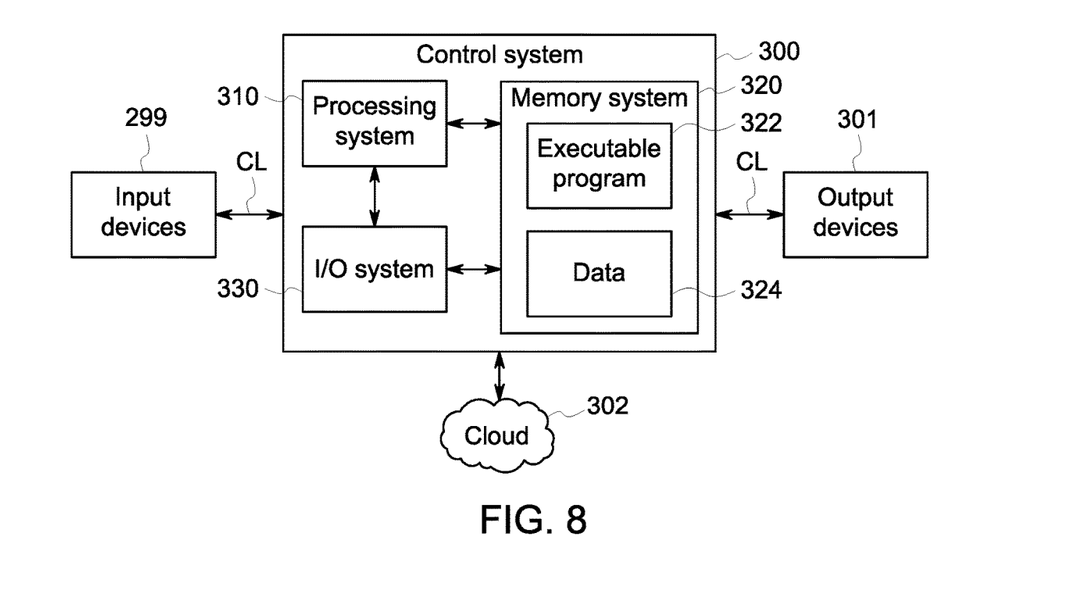
FIG. 8 is a schematic of an exemplary control system for operating the medical device according to the present disclosure.

In certain examples, the control system 300 communicates with each of the one or more components of the system 1 via a communication link CL, which can be any wired or wireless link. The control system 300 is capable of receiving information and/or controlling one or more operational characteristics of the system 1 and its various sub-systems by sending and receiving control signals via the communication links CL. In one example, the communication link CL is a controller area network (CAN) bus; however, other types of links could be used. It will be recognized that the extent of connections and the communication links CL may in fact be one or more shared connections, or links, among some or all of the components in the system 1. Moreover, the communication link CL lines are meant only to demonstrate that the various control elements are capable of communicating with one another, and do not represent actual wiring connections between the various elements, nor do they represent the only paths of communication between the elements. Additionally, the system 1 may incorporate various types of communication devices and systems, and thus the illustrated communication links CL may in fact represent various different types of wireless and/or wired data communication systems.

The control system 300 may be a computing system that includes a processing system 310, memory system 320, and input/output (I/O) system 330 for communicating with other devices, such as input devices 299 and output devices 301, either of which may also or alternatively be stored in a cloud 302. The processing system 310 loads and executes an executable program 322 from the memory system 320, accesses data 324 stored within the memory system 320, and directs the system 1 to operate as described in further detail below.

The processing system 310 may be implemented as a single microprocessor or other circuitry, or be distributed across multiple processing devices or sub-systems that cooperate to execute the executable program 322 from the memory system 320. Non-limiting examples of the processing system include general purpose central processing units, application specific processors, and logic devices.

The memory system 320 may comprise any storage media readable by the processing system 310 and capable of storing the executable program 322 and/or data 324. The memory system 320 may be implemented as a single storage device, or be distributed across multiple storage devices or sub-systems that cooperate to store computer readable instructions, data structures, program modules, or other data. The memory system 220 may include volatile and/or non-volatile systems, and may include removable and/or non-removable media implemented in any method or technology for storage of information. The storage media may include non-transitory and/or transitory storage media, including random access memory, read only memory, magnetic discs, optical discs, flash memory, virtual memory, and non-virtual memory, magnetic storage devices, or any other medium which can be used to store information and be accessed by an instruction execution system, for example.

Through experimentation and development, the present inventors have particularly designed an electrical connector 50 for use with NMT. In this use context, a small current is delivered to the patient to cause a muscle contraction, which is then measured through EMG-specific electrodes 42. In this example, the electrical connector 50 may be configured to both deliver stimulating current to the patient and to communicate back the EMG signal from the patient to the host device 32. However, different embodiments of electrical connectors 50 could be configured to provide additional functions (beyond different medical uses, such as EEG, ECG), for containing identification/counterfeit protection smart chips that would then transmit digital data over the electrical connector 50 for authentication by the host device 32, for example. Moreover, the electrical connector 50 may include an additional pin (exposed contact 23) dedicated to accommodate different sensor types, such as an NMT MechanoSensor that uses Piezo element to measure the muscle contraction instead of using EMG.

In addition or in the alternative, additional fingers 70 may be provided to function as a sensor detection pin for the host device 32 to recognize the electrical connector 50. In certain examples, a sheet sensor such as a GE Entropy EasyFit Sensor or another sensor with electrical conductors and insulation printed on a plastic sheet mates with an interconnect cable that has a receptable for the finger connector. In the interconnect cable there is an identification wire, and when the sensor completes the circuit from the identification wire the monitor will detect that the sensor is connected to the interconnect cable. The interconnect cable may thus serve as an extension between the host device 32 and the peripheral device 40. In this manner, the present disclosure contemplates electrical connector 50 that are connectable as interconnect cables between the host device 32 and the peripheral device 40, that are integrally formed with the host device 32 and connectable to an interconnect cable and/or a peripheral device 40, or that are integrally formed with the peripheral device 40 and connectable to an interconnect cable and/or a host device 32.

The functional block diagrams, operational sequences, and flow diagrams provided in the Figures are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

This written description uses examples to disclose the invention, including the best mode, and also to enable any person skilled in the art to make and use the invention. Certain terms have been used for brevity, clarity, and understanding. No unnecessary limitations are to be inferred therefrom beyond the requirement of the prior art because such terms are used for descriptive purposes only and are intended to be broadly construed. The patentable scope of the invention is defined by the claims and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

What is claimed is:

1. An electrical connector for a medical device, the connector comprising:
   a main support having a front and a back opposite the front, a top and a bottom opposite the top, and a left and a right opposite the left;
   fingers that each extend forwardly from the front of the main support to a tip, wherein the fingers have a top and a bottom opposite the top, and wherein the fingers are arranged from the left to the right of the main support such that gaps are defined between the fingers; and a flexible circuit board having an outer surface and an inner surface opposite the outer surface, wherein the flexible circuit board includes electrical leads on the outer surface thereof, wherein openings are defined through the flexible circuit board between the electrical leads, and wherein the flexible circuit board is wrapped around the fingers such that the outer surface of the flexible circuit board is supported on both the top and the bottom of the fingers and the openings in the flexible circuit board are aligned with the gaps between the fingers;

wherein a finger height is defined between the tops and bottoms of the fingers, further comprising walls that sandwich each of the fingers, wherein the walls each have a top and a bottom opposite the top that define a wall height therebetween, wherein the walls extend away from the main support to a front edge, and wherein at least one of the wall height of each of the walls is greater than the finger height of each of the fingers and the front edges of the walls extends farther than the tips of the fingers from the main support.

2. The connector according to claim 1, wherein the wall height of each of the walls is a height difference greater than the finger height of each of the fingers, and wherein the front edges of the walls extends farther than the tips of the fingers from the main support by a front difference.

3. The connector according to claim 2, wherein the front difference is different than the height difference.

4. The connector according to claim 1, wherein main support walls coupled among the walls are coupled to the left and the right of the main support, the main support walls each having a top and a bottom opposite the top that define a main support wall height therebetween, wherein a main support height is defined between the top and the bottom of the main support, and wherein the main support wall height is greater than the main support height.

5. The connector according to claim 4, wherein the main support walls are coplanar with two of the walls, and wherein the wall heights equal the main support wall heights.

6. The connector according to claim 4, wherein the main support walls extend from the front of the main support only partially towards the back of the main support.

7. The connector according to claim 1, wherein the flexible circuit board has a main section and a moveable section that extends forwardly from the main section to a board edge, the main section being supported by the main support when the flexible circuit board is wrapped around fingers, wherein the openings defined through the flexible circuit board have a front boundary that is closer than the board edge to the main section along the outer surface of the flexible circuit board.

8. The connector according to claim 7, wherein a lock opening is defined through the flexible circuit board, wherein the lock opening is closer than the board edge to the main section along the outer surface of the flexible circuit board, further comprising a lock protrusion extending away from the bottom of the main support, wherein when the flexible circuit board is wrapped around the fingers the lock protrusion of the main support is received within the lock opening defined in the flexible circuit board.

9. The connector according to claim 8, wherein each of the gaps has a gap width between the fingers, wherein the lock opening has a lock opening width extending substantially parallel to the gap widths, and wherein the lock opening width is greater than each of the gap widths.

10. The connector according to claim 1, wherein the electrical leads extend from first to second ends, wherein the first ends are positioned on the fingers when the flexible circuit board is wrapped around the fingers.

11. The connector according to claim 10, wherein each of the electrical leads has an exposed contact between the first and second ends configured for electrically engaging with the medical device, and wherein the exposed contacts are positioned on the tips of the fingers when the flexible circuit board is wrapped around the fingers.

12. The connector according to claim 10, wherein the flexible circuit board has a main section and a moveable section that extends forwardly from the main section to a board edge, the main section being supported by the main support when the flexible circuit board is wrapped around fingers, wherein the openings defined through the flexible circuit board have a front boundary that is closer than the board edge to the main section along the outer surface of the flexible circuit board, and wherein the front boundaries of the openings defined in the flexible circuit board are closer than the first ends of the electrical leads to the board edge.

13. The connector according to claim 1, wherein the fingers comprise at least five fingers that are coplanar with each other and with the main support.

14. The connector according claim 1, wherein the inner surface of the flexible printed circuit board is free of exposed contacts.

15. The connector according to claim 14, wherein the exposed contacts are all a same distance from the front of the main support along the outer surface when the flexible circuit board is wrapped around fingers.

16. A method for making an electrical connector for a medical device, the method comprising:
    forming a main support having a front and a back opposite the front, a top and a bottom opposite the top, and a left and a right opposite the left;
    forming fingers that each extend forwardly from the front of the main support to a tip, wherein the fingers have a top and a bottom opposite the top with a finger height defined therebetween;
    forming walls that sandwich each of the fingers, and wherein the fingers are arranged from the left to the right of the main support such that gaps are defined between the fingers, wherein the walls each have a top and a bottom opposite the top that define a wall height therebetween, wherein the walls each extend away from the main support to a front edge, and wherein the wall height of each of the walls is greater than the finger height of each of the fingers and the front edges of the walls extends farther than the tips of the fingers from the main support;
    forming a flexible circuit board having an outer surface and an inner surface opposite the outer surface to have electrical leads on the outer surface thereof, wherein the flexible circuit board has a main section and a moveable section;
    defining openings through the flexible circuit board between the electrical leads; and
    positioning the main section of the flexible circuit board on the main support and folding the moveable section of the flexible circuit board around the fingers, and wherein the flexible circuit board is wrapped around the fingers such that the flexible circuit board is supported on both the top and the bottom of the fingers and the openings in the flexible circuit board are aligned with the gaps between the fingers.

17. The method according to claim 16, wherein the moveable section of the flexible circuit board extends forwardly from the main section to a board edge, further comprising defining a lock opening through the flexible circuit board to be closer than the board edge to the main section along the outer surface of the flexible circuit board, further comprising forming a lock protrusion that extends away from the bottom of the main support, wherein when the flexible circuit board is wrapped around the fingers the lock protrusion of the main support is received within the lock opening defined in the flexible circuit board, wherein the electrical leads extend from first to second ends, wherein the first ends are positioned on the fingers when the flexible circuit board is wrapped around the fingers, wherein each of the electrical leads has an exposed contact between the first and second ends configured for electrically engaging with the medical device, and wherein the exposed contacts are positioned on the tips of the fingers when the flexible circuit board is wrapped around the fingers.

18. An electrical connector for a medical device, the connector comprising:
- a main support having a front and a back opposite the front, a top and a bottom opposite the top, and a left and a right opposite the left, wherein a lock protrusion extends away from the bottom of the main support;
- fingers that extend forwardly from the front of the main support to a tip, wherein the fingers have a top and a bottom opposite the top, wherein a finger height is defined between the tops and bottoms of the fingers, wherein the fingers are arranged from the left to the right of the main support such that gaps are defined between the fingers, and wherein the fingers are coplanar with each other and with the main support;
- walls that sandwich each of the fingers, wherein the walls each have a top and a bottom opposite the top that define a wall height therebetween, wherein the walls extend away from the main support to a front edge, and wherein at least one of the wall height of each of the walls is greater than the finger height of each of the fingers and the front edges of the walls extends farther than the tips of the fingers from the main support, wherein the wall height of each of the walls is greater than the finger height of each of the fingers, and wherein the front edges of the walls extends farther than the tips of the fingers from the main support; and
- a flexible circuit board having an outer surface and an inner surface opposite the outer surface, wherein the flexible circuit board has a main section and a moveable section that extends forwardly from the main section to a board edge, wherein the flexible circuit board includes electrical leads that are exposed on the outer surface thereof, wherein openings are defined through the flexible circuit board between the electrical leads, and wherein the flexible circuit board is wrapped around the fingers such that the outer surface of the flexible circuit board is supported on both the top and the bottom of the fingers and the openings in the flexible circuit board are aligned with the gaps between the fingers, wherein a lock opening is defined through the flexible circuit board, wherein the lock opening is closer than the board edge to the main section along the outer surface of the flexible circuit board, wherein when the flexible circuit board is wrapped around the fingers the lock protrusion of the main support is received within the lock opening defined in the flexible circuit board.

* * * * *